(12) United States Patent
Ma (10) Patent No.: US 7,863,895 B2
(45) Date of Patent: Jan. 4, 2011

(54) SYSTEM, PROGRAM PRODUCT, AND METHOD OF ACQUIRING AND PROCESSING MRI DATA FOR SIMULTANEOUS DETERMINATION OF WATER, FAT, AND TRANSVERSE RELAXATION TIME CONSTANTS

(75) Inventor: Jingfei Ma, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 250 days.

(21) Appl. No.: 11/919,937

(22) PCT Filed: May 4, 2006

(86) PCT No.: PCT/US2006/017349

§ 371 (c)(1),
(2), (4) Date: Jun. 9, 2008

(87) PCT Pub. No.: WO2006/121827

PCT Pub. Date: Nov. 16, 2006

(65) Prior Publication Data

US 2009/0093704 A1    Apr. 9, 2009

(51) Int. Cl.
*G01V 3/00* (2006.01)
(52) U.S. Cl. .................................................. 324/309
(58) Field of Classification Search ......... 324/300–322; 600/410–435
See application file for complete search history.

(56) References Cited

U.S. PATENT DOCUMENTS

| | | | |
|---|---|---|---|
| 5,055,790 A * | 10/1991 | Siuciak et al. ............... | 324/309 |
| 5,270,654 A | 12/1993 | Feinberg et al. | |
| 5,594,336 A | 1/1997 | Gullapalli et al. | |
| RE35,656 E | 11/1997 | Feinberg et al. | |
| 5,909,119 A | 6/1999 | Zhang | |
| 6,016,057 A | 1/2000 | Ma | |
| 6,263,228 B1 * | 7/2001 | Zhang et al. ................. | 600/409 |
| 6,459,922 B1 | 10/2002 | Zhang | |
| 6,614,225 B1 * | 9/2003 | Feinberg ...................... | 324/307 |

(Continued)

OTHER PUBLICATIONS

J. Ma, "A Single-Scan Imaging Technique for Measurement of the Relative Concentrations of Fat and Water Protons and Their Transverse Relaxation Time," Journal of Magnetic Resonance 125, pp. 92-101 (1997).

*Primary Examiner*—Melissa J Koval
*Assistant Examiner*—Dixomara Vargas
(74) *Attorney, Agent, or Firm*—Bracewell & Giuliani LLP (57) ABSTRACT

A system, program product, and method to determine water, fat, and transverse relaxation time constants in MRI scanning are provided. A method includes initiating readout gradient pulses to collect echo signals with identical phase encoded gradients to thereby produce a plurality of images, instead of a single image with a single readout gradient. A receiver bandwidth used for collecting the echo signals can be determined responsive to an acquisition matrix size along the readout axis and a time duration for water and fat signals to evolve by a preselected phase angle. In a modified FSE implementation, for example, a method includes using readout gradient pulses that use substantially all of the echo spacing time periods between successive refocus RF pulses. By exploiting the phase and the amplitude relationship between the images, the method can include processing the images to generate separate water and fat images, as well as quantitative maps of transverse relaxation time constants.

7 Claims, 8 Drawing Sheets

U.S. PATENT DOCUMENTS 6,842,000 B2 * 1/2005 Norris et al. ............... 324/309
6,856,134 B1   2/2005 Reeder
2003/0123056 A1   7/2003 Barnes et al.
2004/0064032 A1 * 4/2004 Ma ........................... 600/410

* cited by examiner

SYSTEM, PROGRAM PRODUCT, AND METHOD OF ACQUIRING AND PROCESSING MRI DATA FOR SIMULTANEOUS DETERMINATION OF WATER, FAT, AND TRANSVERSE RELAXATION TIME CONSTANTS

BACKGROUND OF THE INVENTION

1. Field of the Invention

The present invention relates to the medical industry and magnetic resonant imaging (MRI) and, more particularly, to MRI and systems, program product, and methods for acquiring data using a modified data acquisition strategy and for processing the data to simultaneously determine separate chemical species (such as water and fat) and their transverse relaxation time constants.

2. Description of Related Art

Magnetic resonance imaging (MRI) systems have become well known and well used in the field of medical diagnostics. For example, MRI is a useful tool for detecting and characterizing brain tumors and can be more sensitive and specific than other competing modalities such as X-ray computed tomography (CT) or ultrasound sonography. Over the two past decades, improvements in hardware technology and data acquisition/processing techniques for MRI examinations have permitted drastically higher-quality images to be produced in a relatively short time. As a result, diagnostic images with varying degrees of resolution are available to the radiologist that can be adapted to particular diagnostic applications.

In general, MRI examinations are based on the interactions among a primary magnetic field, a radio frequency (RF) magnetic field and time varying magnetic gradient fields with nuclear spins within the subject of interest. Specific nuclear components, such as hydrogen nuclei in water molecules, have characteristic behaviors in response to external magnetic fields. The precession of spins of such nuclear components can be carefully manipulated through RF and gradient fields, detected with an RF coil, and processed to reconstruct a useful image.

Conventionally, as understood by those skilled in the art, the magnetic fields used to generate images in MRI systems include a highly uniform, static magnetic field that is produced by a primary magnet. A series of gradient fields are produced by a set of gradient coils disposed around the subject. The gradient fields encode positions of individual volume elements or voxels in three dimensions. An RF coil is employed to produce an RF field. This RF field perturbs the spin system from its equilibrium or aligned direction and causes the spins to process around the axis of their equilibrium magnetization. As nuclei of high energy state relax and realign, emitted energy can provide information about the surroundings or environment of the nuclei. The realignment along the magnetic field is known as longitudinal relaxation, and the time in milliseconds (ms) required for a certain percentage of the nuclei to realign is known as T1. In turn, the transverse relaxation refers to the process by which the transverse component of the magnetization decays to zero, and the time constant is known as T2. During this precession, free-induction decay (FID) signals are generated by the spins and are detected by either the same transmitting RF coil or by a separate receive-only coil. These signals are amplified, filtered, and digitized. The digitized signals are then processed using one of several possible reconstruction algorithms to reconstruct a useful image.

Many specific techniques have been developed to acquire magnetic resonance (MR) images for a variety of applications. One major difference among these techniques is in the way gradient pulses and RF pulses are used to manipulate the spin systems to yield different image contrasts, signal-to-noise ratios (SNR's), and resolutions. Graphically, such techniques are illustrated as "pulse sequences" in which the pulses are represented, along with temporal relationships among them. In recent years, pulse sequences have been developed which permit extremely rapid acquisition of large amounts of raw data. Such pulse sequences permit significant reduction in the time required to perform the patient examinations. Time reductions are particularly important for acquiring high-resolution images, as well as for suppressing motion effects and reducing the discomfort of patients in the examination process.

The most widely used data acquisition and processing techniques on modern day MRI scanners are Fourier or spin warp-based. With this approach, raw data required to reconstruct an image are collected sequentially line-by-line and placed on a rectilinear coordinate. Each line of data is referred to as frequency encoding and is collected while a frequency-encoding gradient is turned on. A phase encoding gradient of varying areas is applied before the frequency-encoding gradient to advance between different frequency encoding lines and to complete the filling of the rectilinear coordinates. After raw data are complete, simple fast Fourier transform can be applied to produce a spatial image.

The duration of the frequency encoding gradient is determined by the acquisition matrix size (Xres) along the frequency encoding direction and the receiver bandwidth, both of which are independently selected by an operator. The image resolution along the frequency encoding direction is simply determined by Xres, and the field-of-view (FOV). Typically, the higher the receiver bandwidth, the lower the signal-to-noise ratio (SNR) for the final image. On the other hand, higher receiver bandwidth leads to an image with less geometric distortion due to background field inhomogeneity and signal decay during the frequency encoding time. Another factor that needs to be considered when choosing a receiver bandwidth is that the higher the receiver bandwidth, the higher the amplitude for the frequency encoding gradient is needed. The maximum amplitude of the gradient that is available on an MRI scanner is limited and typically is within the range of 1 to 4 Gauss/cm.

Among the pulse sequences, which have been developed for fast acquisition of large amounts of MR data, is a sequence generally referred to as fast spin echo (FSE or RARE). This technique is capable of generating high-quality image data in a fraction of the time needed for conventional spin echo imaging. FSE techniques have thus become the sequence of choice, especially for T2-weighted imaging. For example, a simplified graphical diagram of an FSE pulse sequence is illustrated in prior art FIG. 2. As shown, the time available for acquiring echo signals between each 180° RF refocus pulse pair is known as echo spacing (esp). During each esp, a readout or frequency-encoding gradient pulse (gxw), having an area equal to twice the area of an initial dephasing gradient pulse (gx1), is applied to acquire echo signals. Each of the echo signals constitutes a line of the raw data in the rectilinear coordinate and is encoded differently with other phase encode gradients (not shown in FIG. 2) to form other lines of data necessary for a final image.

Perhaps a prominent and distinguishing feature of FSE images, however, is an anomalously bright signal resulting from fat content in the tissue being imaged. The phenomenon has been attributed to the demodulation of the J-coupling and de-sensitization of diffusion through inhomogeneities due to the rapidly refocusing RF pulse trains contained in the FSE pulse sequence.

Because fat often obscures lesion detection, separation of water and fat in MRI can be important. Fat suppression has therefore become desirable in T2-weighted, high-resolution imaging procedures. At present, several techniques have been employed for such fat suppression. A first such technique is referred to as chemical saturation, and can be used to reduce the fat signal, but requires very homogeneous magnetic fields due to the close separation of the water and fat signals in their resonance frequencies. In particular, the RF pulse must saturate all fat, requiring a highly uniform main magnetic field, to avoid residual fat signals. Similarly, the technique depends highly upon the homogeneity of the RF field, which is needed to achieve an accurate flip of the fat signal for suppression and subsequent flip of the resulting water signals for imaging. Inhomogeneity in the main magnetic field is particularly a problem at locations off the isocenter of the field system. Finally, patient anatomy also tends to perturb the fields, rendering the technique particularly problematic.

A second technique that has been developed for fat suppression involves short inversion time (TI) inversion recovery, and is commonly referred to as STIR. This technique is intended to flip all signals to an inverted direction, with fat and water signals recovering at different rates. The technique then acquires the image data when the fat signal is crossing the null point while the water signal is still partially in the inverted state. Because of its underlying principles, the technique typically is dependent on the T1 of the water signal and, generally, results in relatively low SNR due to the partial recovery of the water signal during the recovery of the fat signal.

A further technique that has been developed is generally referred to as the Dixon technique. In this approach, the chemical shift difference between water and fat is encoded into images with different echo shifts. Field inhomogeneity effects appear as image phase errors, which in principle can be corrected for by a combination of multipoint acquisition and more elaborate image processing. Although these techniques allow for more uniform water and fat separation in the presence of field inhomogeneity, one clear drawback is the requirement for multiple data acquisitions and, therefore, longer scan times.

Incorporating the Dixon approach with fat suppression into FSE pulse sequences presents a mutually beneficial combination. Although the Dixon technique provides a potentially robust separation of the strong fat signal, FSE helps to alleviate for long data acquisition times in the multipoint Dixon technique. In a combination of these techniques, however, echo shift as dictated by the Dixon technique is usually achieved by shifting the timing of the readout gradient and the data acquisition window to maintain necessary conditions (Carr-Purcell-Meiboom-Gill; "CPMG" conditions). As a result, inter-echo spacing can increase, leading to substantial loss in the slice coverage for a given sequence repetition time, largely offsetting the gain of using FSE for reducing the scan time. The technique is believed, therefore, to be appropriate for imaging small anatomic areas only that do not require large slice coverage.

Dixon techniques based on the conventional spin echo or gradient echo sequences generally employ shifting the echo through either shifting the RF pulse or the readout gradient/data acquisition window. In the case of FSE based Dixon techniques, the CPMG condition dictates that only the latter strategy can be used. Shifting the readout gradient/data acquisition window, however, would require increasing the echo spacing, leading to the disadvantage of longer acquisition times and less slice coverages because of the increased dead time during a sequence. Consequently, the loss of slice coverage for a given scan time, or increased scan time for a given number of slices, and an increase in image blurring and greater sensitivity to flow and motion artifacts, can all result.

Accordingly, there is a need, therefore, for enhanced techniques for obtaining shifts in echoes in MR imaging sequences. There is a particular need for an FSE-based Dixon imaging approach, which achieves the echo shifts satisfying the CPMG conditions without necessitating an increase in echo spacing. There is, at present, a particular need for technique, which can be implemented on existing hardware and control systems to obtain enhanced timing and imaging clarity in a relatively straightforward manner. Also, there is a need for data acquisition techniques that enhance fat quantitation, such as for use in diagnosis for various diseases, such as bone marrow disorders, adrenal tumors, or hepatic steatosis.

There, further, is still a need for enhanced MRI data acquisition techniques which enhance quantitation of transverse relaxation time constants to thereby be used for lesion characterization, tissue iron concentration measurement, and monitoring of progression of neurological diseases, such as Parkinson's disease. Additionally, the effective transverse relaxation ($T2^*$) can be broken into an RF reversible ($T2'$) component and an RF irreversible ($T2$) component. Traditionally, measurement of the transverse relaxation time constants is performed by acquiring a series of gradient echoes, or more conveniently a series of FSE echoes with different echo times. These prior approaches, however, usually require very long scan times, and at most measure only one component of the transverse relaxation at a time. Also, these measurements are subject to errors in the RF flip angles or slice profiles. Still further, there is a need for enhanced MRI data acquisition techniques that reduce the time and increase the accuracy of quantitation of transverse relaxation time constants.

SUMMARY OF THE INVENTION

In view of the foregoing, embodiments of a system, program product, and methods according to the present invention beneficially provide enhanced timing and image clarity on conventional magnetic resonant imaging (MRI) systems. Embodiments of a system, program product, and methods enhance acquiring data to more efficiently determine or separate water and fat in MRI images, including MRI of larger anatomic areas and areas that require large slice coverage. Embodiments of a program product and methods also beneficially enhance determination of transverse relaxation time constants in a single MRI scan. Embodiments of a program product and methods further beneficially take advantage of some of the benefits of fast spin echo (FSE) and Dixon techniques by using a modified FSE Dixon data acquisition to significantly enhance efficiency and image clarity. Embodiments of systems, methods, and program products of the present invention still further beneficially provide MRI data acquisition, which enhances more accurate and less time consuming determination of water, fat, and transverse relaxation time constants.

More particularly, an embodiment of a method of acquiring data in a single MRI scan, for example in the case of FSE, includes initiating readout gradient pulses during an echo spacing (esp) time period. The gradient pulses have a plurality of gradient polarities that use substantially all of the esp time period. In this manner, for example, maximum data efficiency can be used, if desired, so that little or no dead space exists between echo spacings such as in FSE pulse sequence. The method can also include collecting a plurality of echo signals during the esp time period responsive to the plurality of readout gradient pulses, and the plurality of echo signals also are generated to use substantially all of the esp time period.

An embodiment of a method of acquiring data in a single MRI scan includes using a plurality of readout gradients in lieu of a single readout gradient to collect a single line of raw data with identical phase encoded gradient. The embodiment further includes selecting an image field-of-view (FOV) and the acquisition matrix size along the readout direction (Xres) such as by an operator of an MRI system. The embodiment also includes determining an appropriate receiver bandwidth such that the time separation between the successive readouts of the plurality of readout gradients causes water and fat signals to evolve by a preselected phase angle. For example, at a 1.5-Tesla field strength, and an Xres of 256 points or pixels, the time separation may be chosen to be approximately 2.3 millisecond, which will cause water and fat signals to evolve out of phase by 180°. The corresponding receiver bandwidth required to achieve such a time separation is about ±62.5 kHz. Conversely, at 3.0 Tesla field strength and an Xres of 256 pixels, the time separation may be chosen to be approximately 3.45 milliseconds, which will cause water and fat signals to evolve out-of-phase by 540°. The corresponding receiver bandwidth required to achieve such a time separation is about ±42 kHz. The embodiment further includes processing the plurality of complex images from the plurality of the readout gradients to generate separate water and separate fat images, as well as quantitative maps of the transverse relaxation time constants.

Another embodiment of a method of acquiring data in a single MRI scan, for example in the case of FSE, includes initiating an initial dephasing gradient pulse along a readout gradient axis prior in time to an occurrence of a first radio frequency (RF) refocus pulse being initiated along an RF axis. The initial dephasing gradient pulse has a first gradient area defined by the product of amplitude of the dephasing pulse and a time duration (or duration) of the dephasing pulse. The method also includes initiating a plurality of readout gradient pulses later in time than the first RF refocus pulse. The lapse of time between the first RF refocus pulse and the second RF refocus pulse defines an echo spacing (esp) time period. Each of the plurality of readout gradient pulses has a second gradient area also defined by the product of an amplitude of the readout gradient pulse and a time duration (or duration) of the same readout gradient pulse. An absolute value of the second gradient area being equal to two times the first gradient area. The method can further include collecting a plurality of echo signals during the esp time period responsive to the plurality of readout gradient pulses. Each of the plurality of echo signals corresponds to one of the plurality of readout gradient pulses.

Yet another embodiment of the present invention provides a program product stored in a tangible computer medium to be operable on a computer, the program product operating to perform the steps of (a) initiating the gradient pulses during an echo spacing (esp) time period, the gradient pulses shaving a plurality of gradient polarities that use substantially all of the esp time period and (b) collecting a plurality of echo signals during the esp time period responsive to the plurality of readout gradient pulses, each of the plurality of echo signals corresponding to one of the plurality of readout gradient pulses, and the plurality of echo signals likewise being generated to use substantially all of the esp time period.

Still another embodiment of the present invention provides a program product stored in a tangible computer medium to be operable on a computer, the program product, e.g., such as by a type of or an embodiment of a sequence initiator, operating to perform the step of initiating an initial dephasing gradient pulse along a readout gradient axis prior in time to an occurrence of a first radio frequency (RF) refocus pulse being initiated along an RF axis. The initial dephasing gradient pulse has a first gradient area defined by the product of an amplitude of the dephasing pulse and a time duration of the dephasing pulse. The operating also including the step of initiating a plurality of readout gradient pulses later in time than the first RF refocus pulse and prior in time to a second RF refocus pulse. The lapse of time between the first RF refocus pulse and the second RF refocus pulse defines an echo spacing (esp) time period, and each of the plurality of readout gradient pulses has a second gradient area also defined by the product of an amplitude of the readout gradient pulse and a time duration of the same readout gradient pulse. The area of the dephasing gradient has a definite relationship to the area of each of the plurality of readout gradient pulses. For example, an absolute value of each of the plurality of the readout gradient pulses is substantially equal to each other and to about two times the area of the dephasing gradient. The operating steps can further include collecting a plurality of echo signals during the esp time period responsive to the plurality of readout gradient pulses. Each of the plurality of echo signals corresponds to one of the plurality of readout gradient pulses. This can then be repeated for each of a plurality of RF refocus pulse pairs in an FSE echo train.

Yet still a further embodiment of a system to acquire data in a single magnetic resonant imaging (MRI) scan according to the present invention is provided. An embodiment of the system includes an MRI device adapted to provide an MRI scan of a subject, a controller associated with the MRI device to control the scanning of the MRI device, and memory associated with the controller and having program product stored therein. The program product operates to perform the steps of: initiating an initial dephasing gradient pulse along a readout gradient axis prior in time to an occurrence of a first radio frequency (RF) refocus pulse being initiated along an RF axis, the initial dephasing gradient pulse having an area defined by the product of an amplitude of the dephasing pulse and a time extent of the dephasing pulse; initiating a plurality of readout gradient pulses later in time than the first RF refocus pulse and prior in time to a second RF refocus pulse, the lapse of time between the first RF refocus pulse and the second RF refocus pulse defining an echo spacing (esp) time period, each of the plurality of readout gradient pulses having an area also defined by the product of an amplitude of the readout gradient pulse and a time extent of the same readout gradient pulse, an absolute value of the area being equal to two times the area of the dephasing gradient (notably, as set forth below herein, the plurality of readout gradient pulses are applied during each esp time period between every successive refocus RF pulse pairs along an FSE echo train (see, e.g., FIG. 3); and (c) collecting a plurality of echo signals during the esp time period responsive to the plurality of readout gradient pulses, each of the plurality of echo signals corresponding to one of the plurality of readout gradient pulses. The embodiment of the system also can include a display responsive to the controller to display one or more magnetic resonant images, and the plurality of echo signals can include a first, a second, and a third echo signal occurring sequentially in time and corresponding to the respective first, second, and the third readout gradient pulses, each of the first, the second, and the third echo signals being phase encoded identically. The program product can further operate to perform the steps of repeating (a) and (b) for each of a plurality of substantially equal and sequential esp time periods between successive RF pulse pairs along an FSE echo train. Each of the plurality of esp time periods is substantially equal to the esp time period. Each set of the first, the second, and the third echo signals is generated between each of the sequential esp time periods. The signals from the sequential time periods are phase coded differently. Raw data corresponding to the three readout gradients are collected, stored and processed to generate separate water and separate fat images, as well as quantitative maps of transverse relaxation time constants.

By beneficially creating or initiating a pulse sequence along the readout gradient axis that has a plurality of pulses, e.g., three pulses, having a relationship to the area of an initial dephasing pulse along the gradient axis and which utilize substantially all of the echo spacing time, —embodiments of a program product and methods significantly enhance efficiency and image clarity. By recognizing the relationship among the echo spacing and the initial dephasing pulse, the pulse sequence advantageously provides MRI data acquisition in a single MRI scan, which is more accurate and less time consuming for determining water, fat, and transverse relaxation time constants. Embodiments of methods, program products, and systems of the present invention also beneficially provide FSE acquisition of both water-only or fat-only images in a simple scan and provide images of both RF irreversible and reversible components of the transverse relaxation rate constants.

BRIEF DESCRIPTION OF THE DRAWINGS

Some of the features and benefits of the present invention having been stated, others will become apparent as the description proceeds when taken in conjunction with the accompanying drawings, in which.

DETAILED DESCRIPTION

The present invention now will be described more fully hereinafter with reference to the accompanying drawings in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

As illustrated in FIGS. 1 and 3-7, embodiments of methods, program products, and systems according to the present invention can beneficially use a data acquisition technique or method that modifies, for example, the well known FSE pulse sequence. In an MRI system 10, an MRI machine 11, such as shown and as understood by those skilled in the art, includes a primary magnetic field, a radio frequency (RF) field and time varying gradient fields. Such a machine 11 can be a closed or an open MRI machine by any number of manufacturers as understood in the art. A controller 13 associated with the MRI machine 11 and/or a computer 15 (including peripherals such as display(s) and printer(s)) assist in operating the machine and enhanced FSE data acquisition program product 20 or software, for example, can be stored in memory of the controller 13 or on a separate computer, computer device, or computer system. Embodiments of an enhanced FSE data acquisition software 20 (see, e.g., FIGS. 6-7), for example, advantageously can initiate a pulse sequence to generate the desired images in a single MRI scan.

Figure 1:
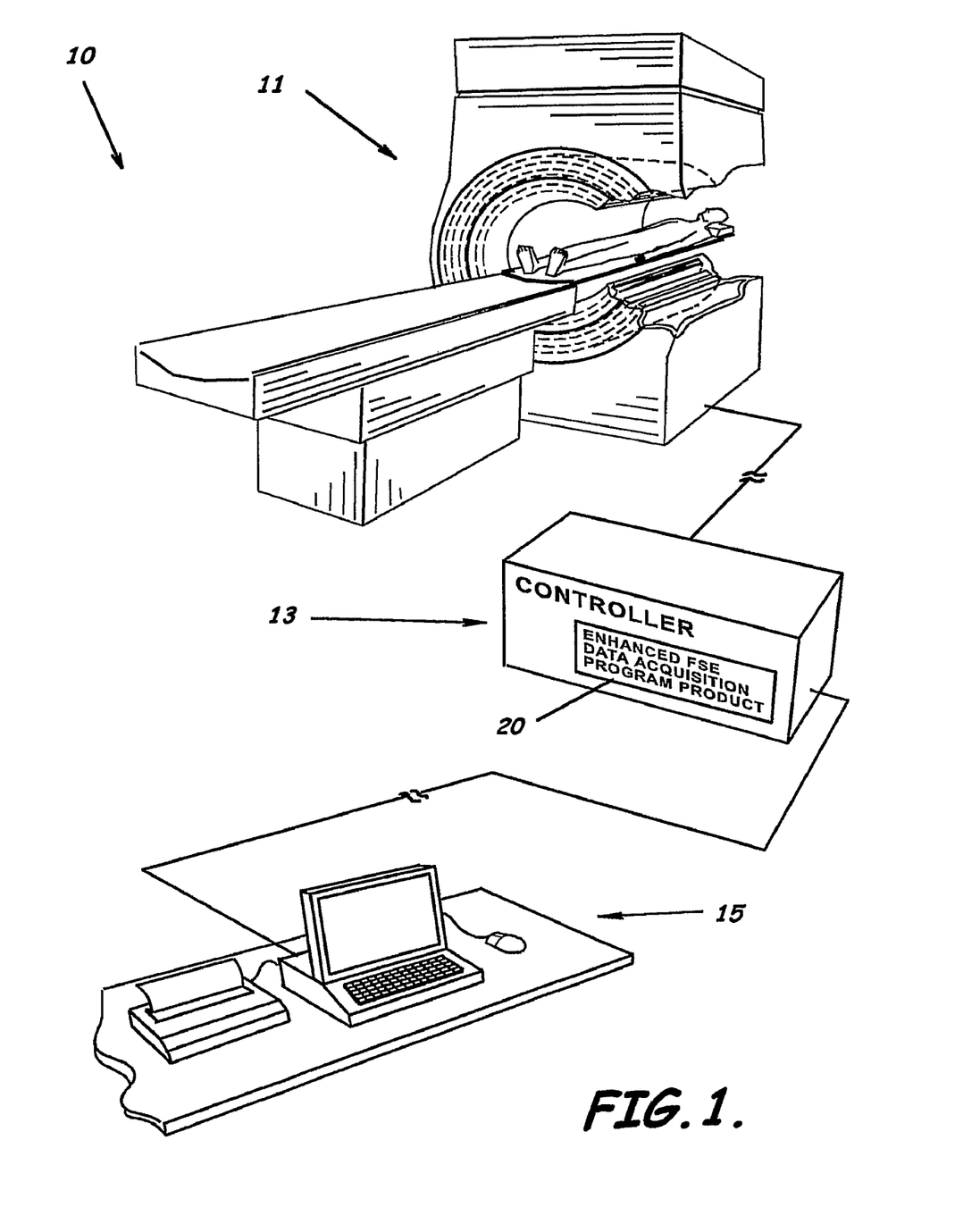
FIG. 1 is a schematic diagram of a magnetic resonance imaging system according to an embodiment of the present invention.
Figure 2:
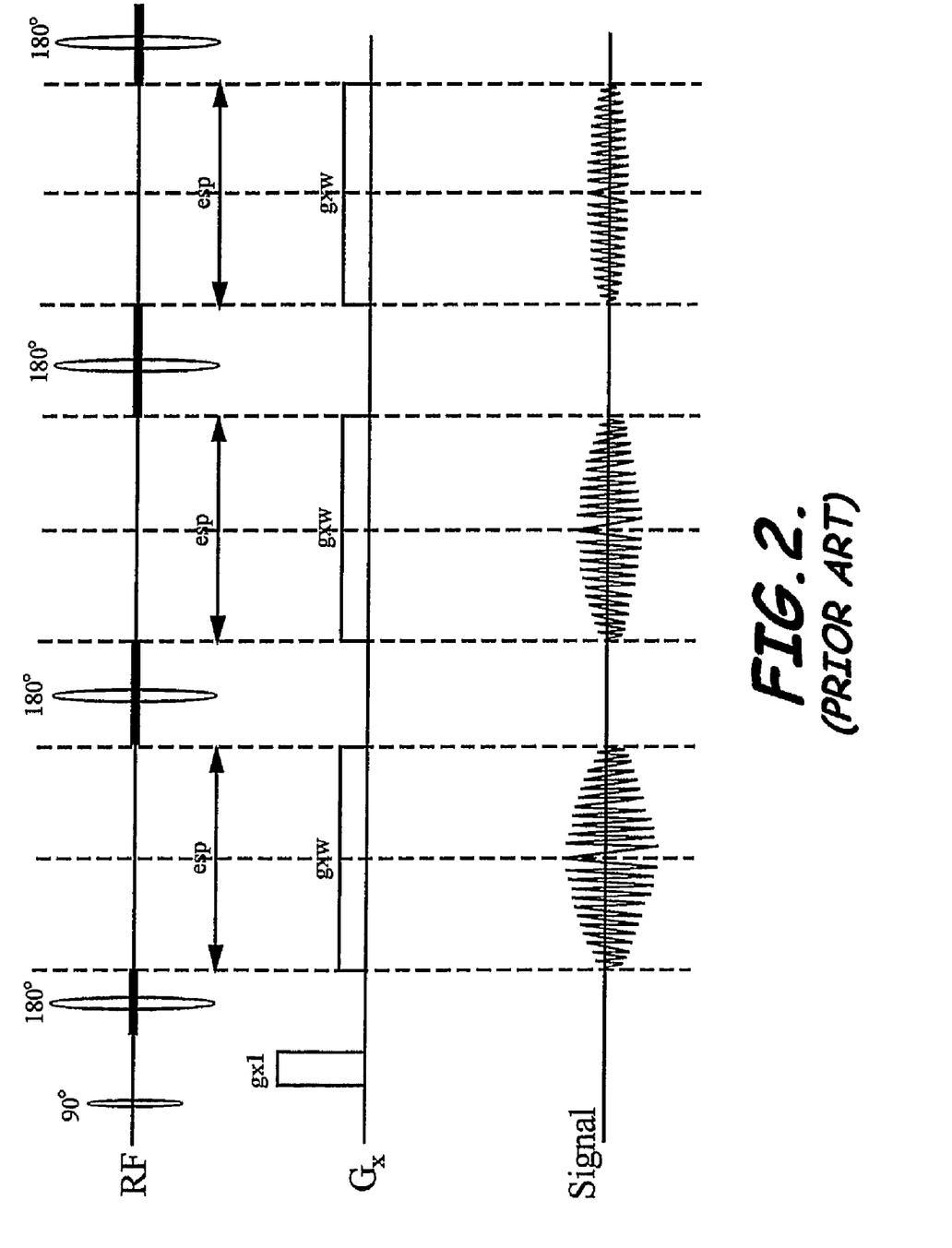
FIG. 2 is a graph of an RF axis, the readout gradient axis, and echo signal axis illustrating the timing relationship of different gradient and RF pulses of the prior art fast spin echo pulse sequence.
Figure 3:
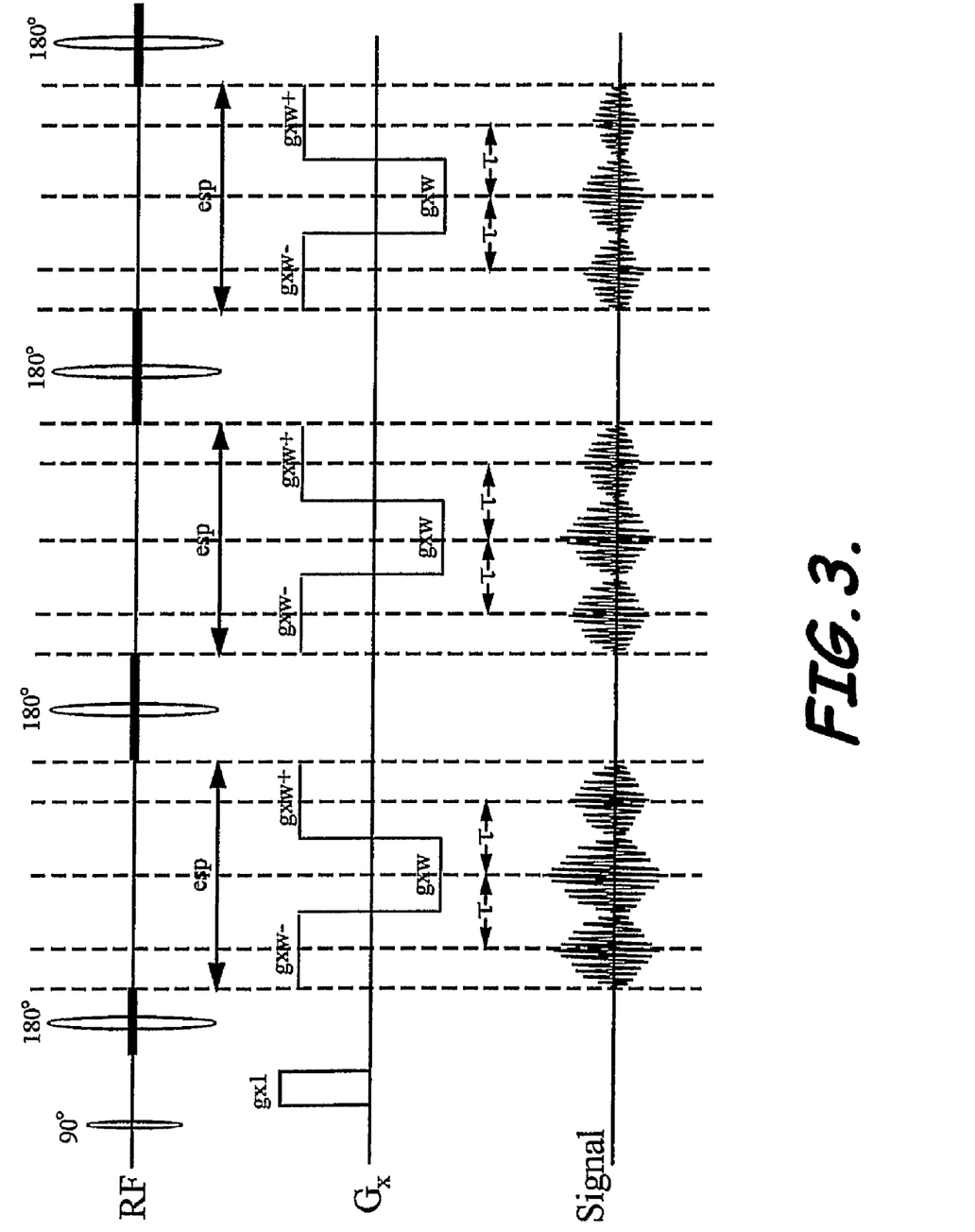
FIG. 3 is a graph of an RE axis, the readout gradient axis, and echo signal axis illustrating the timing relationship of different gradient and RF pulses according to an embodiment of the present invention.

An embodiment of a pulse sequence according to the present invention, for example, is illustrated in FIG. 3. Unlike the prior art, such as shown in FIG. 2 (discussed previously in the Background section of this application), instead of a single gxw pulse, a plurality, e.g., preferably three, of readout gradient pulses (gxw−, gxw, and gxw+) during each esp time period is provided. The areas of gxw− and gxw+ are both about twice the area of gx1. The area of gxw is also about twice the area of gx1, but has the opposite gradient polarity (see FIGS. 4 and 4A). The center of gxw is at the center of esp. Notably, the amplitude (a) of gx1 is often greater than the amplitude of gxw−, gxw (in an opposite gradient polarity), and gxw+ as illustrated. Nevertheless, the amplitude (a) and its product with the pulse time duration ($ts_1$) of the initial dephasing pulse which generally define the area of the gx1 is about one-half the area of each of the plurality of gradient readout pulses gxw−, gxw, gxw+ similarly defined by the product of each of their respective amplitudes (a) and pulse time durations ($ts_2$).

Figure 5:
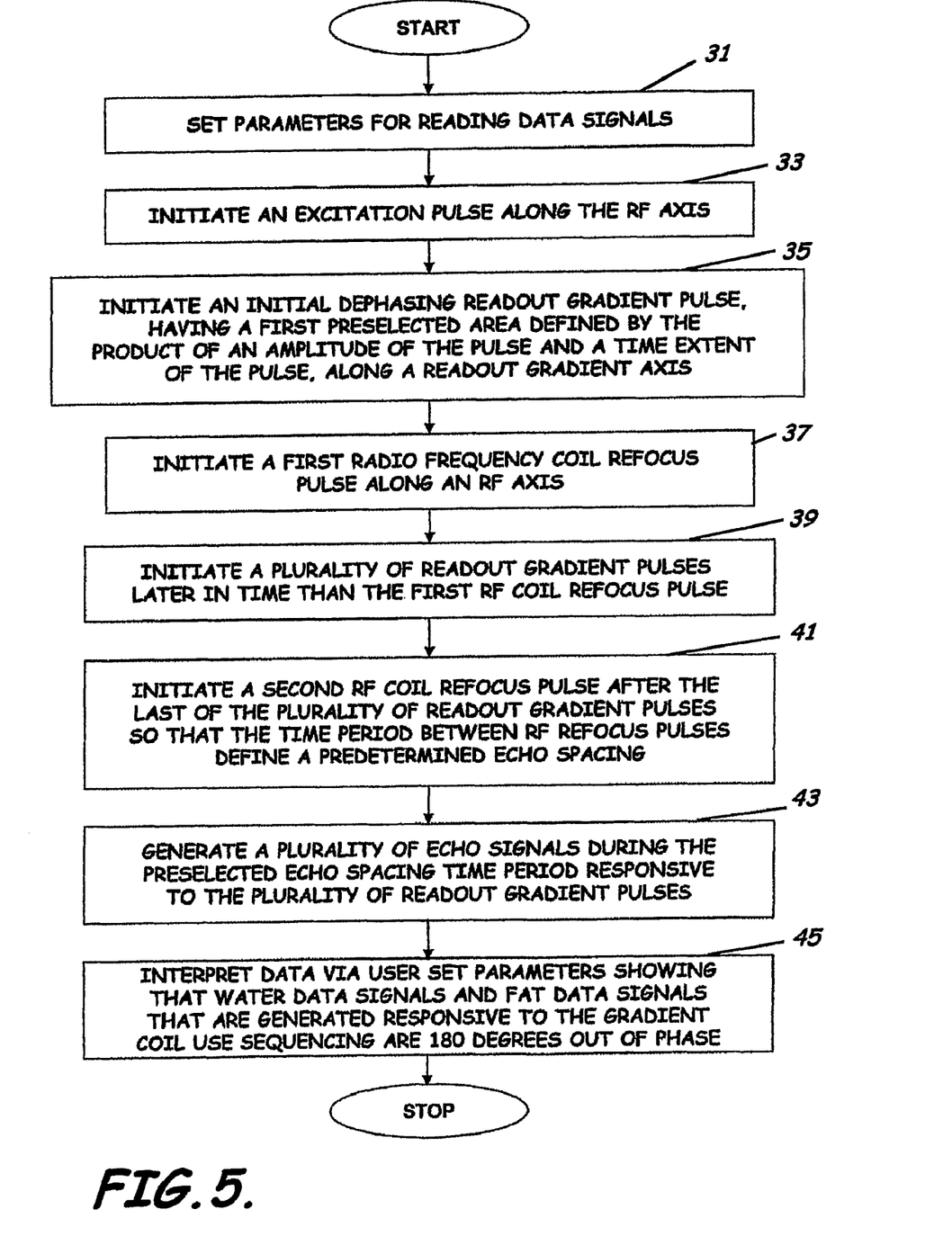
FIG. 5 is a flow diagram of a method of acquiring data to determine the spatial distribution of water, fat, and transverse relaxation time constants according to an embodiment of the present invention.

As illustrated in FIG. 5, for example, an embodiment of a method of acquiring data in a single magnetic resonant imaging (MRI) scan includes initiating a gradient pulse sequence during an echo spacing (esp) time period. The gradient coil of the machine 11, as understood by those skilled in the art, generates a plurality of readout gradient pulses that use substantially all of the esp time period (block 39). The method can also include acquiring a plurality of echo signals during the esp time period responsive to the plurality of readout gradient pulses (block 43). Each of the plurality of echo signals corresponds to one of the plurality of readout gradient pulses, and the plurality of echo signals likewise is generated within the esp time period.

Figures 4, 4A:
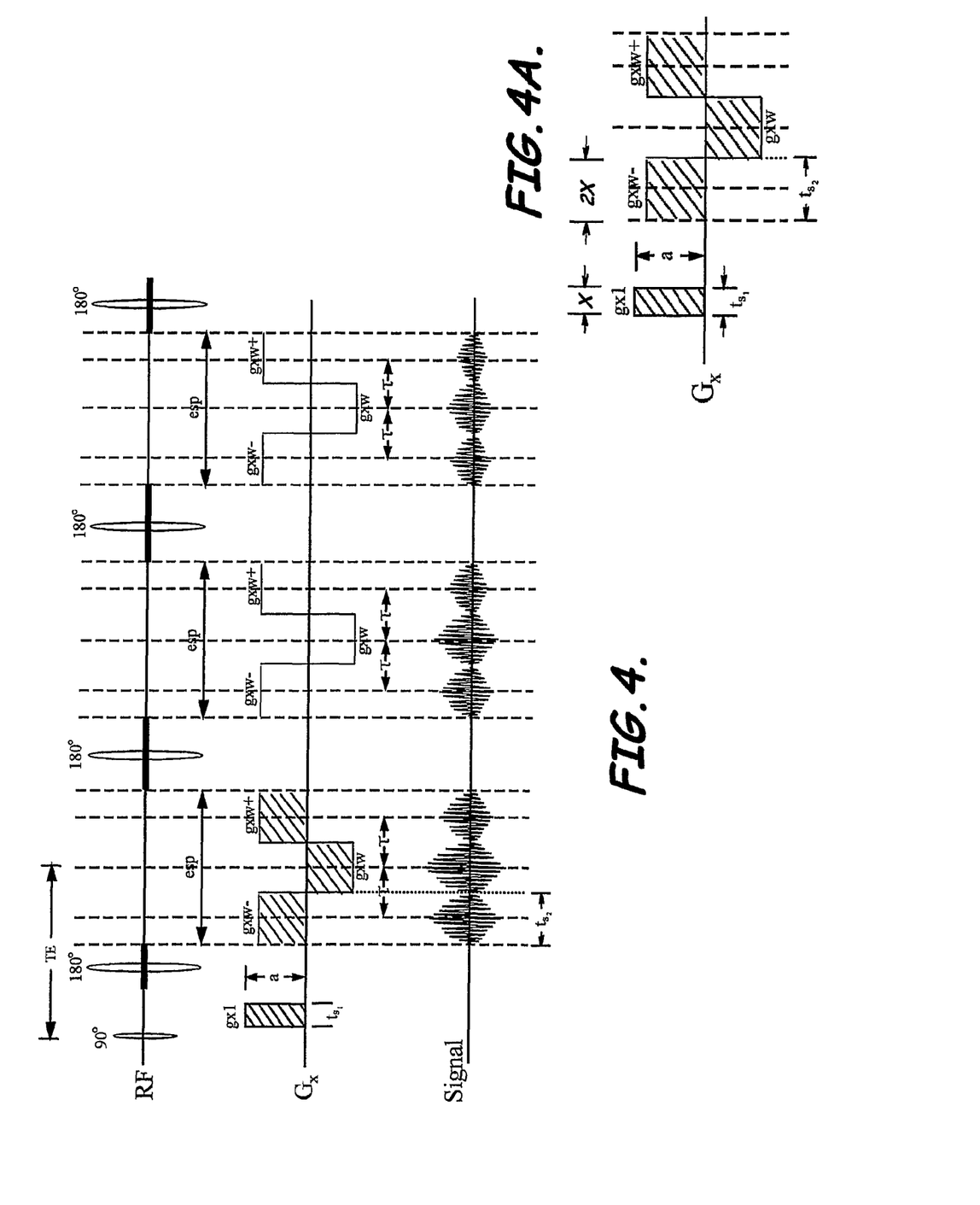
FIG. 4 is a graph of an RF axis, the readout gradient axis, and echo signal axis illustrating the timing relationship of different gradient and RF pulses according to an embodiment of the present invention.
FIG. 4A is a graph of a readout gradient axis further illustrating the relationship between the area and the polarity of the initial dephasing pulse and the area of each of the plurality of gradient pulses according to an embodiment of the present invention.

As shown in FIGS. 3, 4, and 4a, the step of initiating a gradient pulse sequencing, for example, includes initiating an initial dephasing gradient pulse (gx1) along a readout axis, prior in time to occurrence of a first radio frequency (RF) refocus pulse being initiated along an RF axis (block 35). The initial dephasing gradient pulse (gx1) has a first gradient area x defined by the product of an amplitude (a) of the dephasing pulse and a time duration (ts1) of the dephasing pulse (gx1). The method can also include initiating the first RF refocus pulse along the RF axis so that the plurality of readout gradient pulses (gxw−, gxw, gxw+) occur later in time than the first RF refocus pulse (block 37) and initiating a second RF refocus pulse along the RF axis later in time than the occurrence of the plurality of readout gradient pulses (block 41). In this embodiment, for example, the esp time period is defined by an elapse of time between the first RF refocus or 180° pulse and the second RF refocus or 180° pulse.

The method can further include initiating an excitation pulse, e.g., 90° pulse along the RF axis prior in time to the occurrence of the initial dephasing gradient pulse (gx1) and to the occurrence of the first RF refocus pulse (block 33) and, responsive to the generated plurality of echo signals, determining one or more of spatial distribution of water, spatial distribution of fat, and transverse relaxation time constants (block 45). Also, as opposed to the prior art, the receiver bandwidth used to collect the echo signals can be determined based on the acquisition matrix size along the readout direction that an operator selects. The receiver bandwidth is determined such that the time separation between the centers of the successive readout gradients, which is approximately equal to $ts_2$ (FIG. 4A), will cause water and fat signals to evolve by a certain pre-defined phase angle. For example, at a 1.5-Tesla field strength, and an Xres of 256 points, the time separation may be chosen to be approximately 2.3 millisecond, which will cause water and fat signals to evolve out of phase by 180°. The corresponding receiver bandwidth required to achieve such a time separation is about ±62.5 kHz. Conversely, at 3.0 Tesla field strength and an Xres of 256 points, the time separation may be chosen to be approximately 3.45 milliseconds, which will cause water and fat signals to evolve out-of-phase by 540°. The corresponding receiver bandwidth required to achieve such a time separation is about ±42 kHz. The embodiment further includes processing the plurality of complex images from the plurality of the readout gradients to generate separate water and separate fat images, as well as quantitative maps of the transverse relaxation time constants.

Each of the plurality of readout gradient pulses (gxw−, gxw, gxw+), for example, can have a second gradient area 2× (see FIG. 4a) also defined by the product of an amplitude (a) of the readout gradient pulse and a time duration ($ts_2$) of the same readout gradient pulse. An absolute value of the second gradient area 2× substantially equals two times the first gradient area x of the dephasing gradient.

For example, as illustrated in FIGS. 3, 4, and 4A, the plurality of readout gradient pulses can include a respective first (gxw−), a second (gxw), and a third (gxw+) readout gradient pulse occurring almost sequentially in time. The second gradient area 2× of each of the first, the second, and the third readout gradient pulses (gxw−, gxw, gxw+) also is substantially equal. Also, the respective time duration ($ts_2$) of each of the first, the second, and the third readout gradient pulse (gxw−, gxw, gxw+) is substantially equal, and a center of the esp time period substantially corresponds to a center of the second readout gradient pulse. Notably, as understood by those skilled in the art, the shape of the pulses as illustrated in FIGS. 2, 3, 4, and 4A are usually not perfectly rectangular as illustrated. Rather, there is usually a slight upward slope and a slight downward slope for each pulse as defined by the slew rate achievable on a given MR scanner. These pulses, however, are shown in a rectangular format for simplicity and illustrative purposes only.

A time shift between a center of the first readout gradient pulse and the center of the second readout gradient pulse defines a user-selected time shift (τ). A time shift between the center of the second readout gradient pulse and a center of the third readout gradient pulse also substantially equals τ. For example, τ can be set by a user so that water data signals and fat data signals being generated responsive to the gradient pulses of the first and the second readouts, or of the second and the third readouts, are 180 degrees out of phase. At higher magnetic field strength (for example, at 3.0 Tesla), τ can also be more conveniently selected so that the water data signals and the fat data signals being generated responsive to the gradient pulses of the first and the second readouts, or of the second and the third readouts are 540 degrees out of phase. In either case, the first and third readout gradient pulses (gxw−, gxw+) have the same polarity as the initial dephasing gradient pulse (gx1), and the second readout gradient pulse (gxw) has an opposite polarity to the initial dephasing gradient pulse (gx1).

Figure 8:
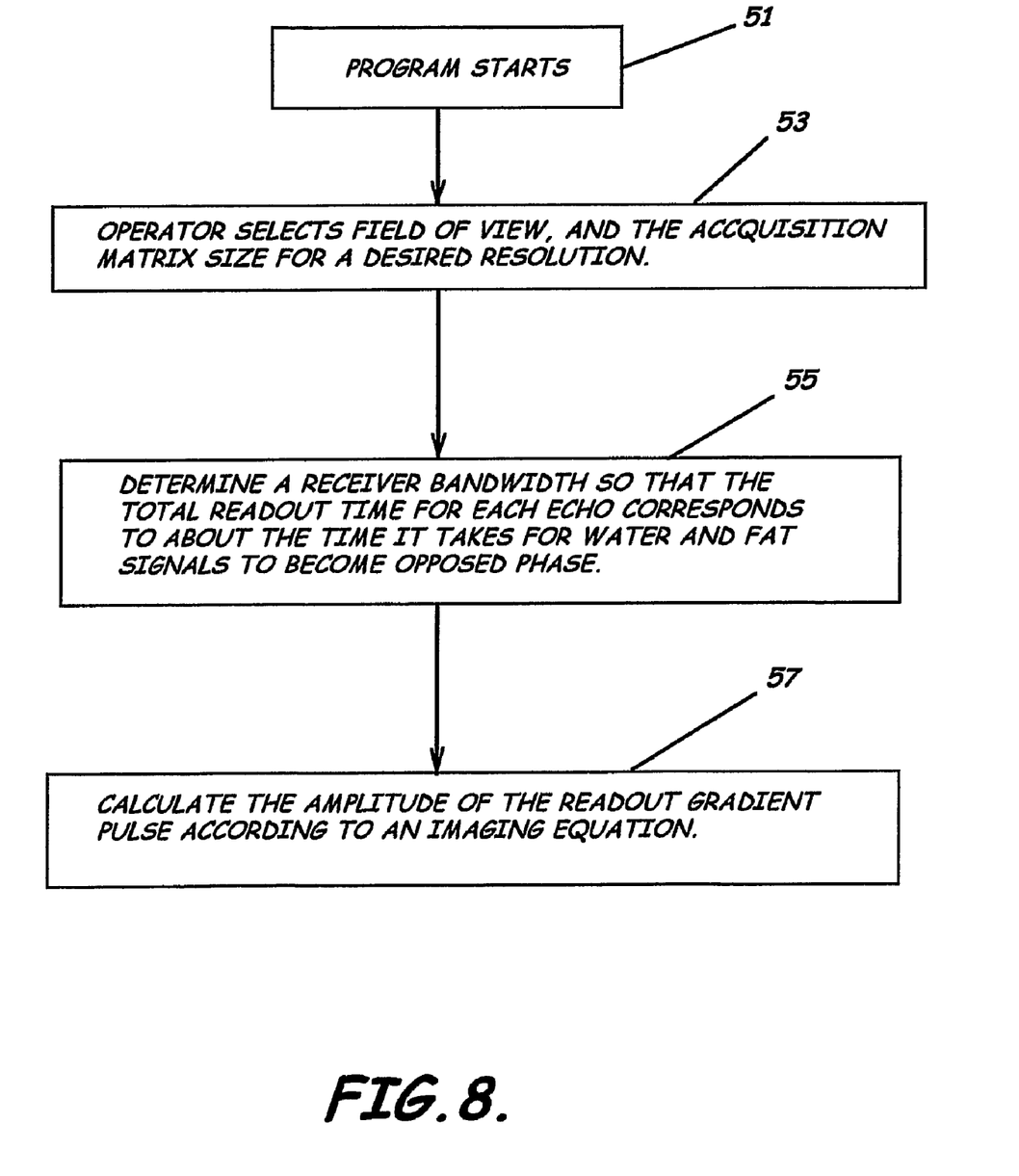
FIG. 8 is a flow diagram of a method of selecting echo spacing so that water and fat signals are out-of-phase for echoes generated during the durations of the first and the third readout gradients according to an embodiment of the present invention.

In conventional fast spin echo (FSE) (prior art), for example, the operator chooses FOV (field of view) of the object to be imaged, the acquisition matrix size (xres), and the receiver bandwidth. The conventional program then calculates the esp, and the time duration and the amplitudes of the dephase gradient, as well as the readout gradient. For an embodiment of a method of the present invention (see FIG. 8), the program control can flow as follows: (1) program starts (block 51); (2) operator selects FOV, and the acquisition matrix size (xres) for a desired resolution (=FOV/xres) (block 53); (3) the program determines a receiver bandwidth (BW) such that the total readout time for each echo corresponds approximately to the time it takes for water and fat signals to become opposed phase (block 55). At 1.5 Tesla field strength, for example, it takes about 2.3 ms for water and fat to evolve 180° out-of-phase. At 3.0 Tesla field strength, it takes about 1.15 ms for water and fat to evolve 180° out-of-phase, and 3.45 ms to evolve 540° out-of-phase. At 1.5 Tesla field strength, if the operator desires xres of 256 points or pixels, then a ±62.5 kHz for receiver bandwidth will make each readout last 2.048 ms (=256/125). Considering it takes 0.1-0.2 ms for the gradient to transition from positive to negative polarity, the time interval between the two successive readouts (defined by the plurality of readout gradients) will be just about 2.3 ms. At 3.0 Tesla field strength, because the time for water and fat to become 180° out of phase is much shorter, if the operator still desires xres=256 points or pixels, then the required bandwidth has to be doubled. This can be done only if the gradient is powerful enough. An alternative solution by an embodiment of a method according to the present invention is to let the program decide the receiver bandwidth on the condition that it takes water and fat to evolve to 540° out-of-phase. In that case, the required bandwidth needs only to be about ±42 kHz; and (4) once the program decides on an optimal bandwidth, it will calculate the amplitude of the readout gradient according to a standard imaging equation (block 57) such as follows:

$$G = \frac{BW}{\gamma FOV},$$

where γ is the gyromagnetic ratio (a constant), as understood by those skilled in the art, and BW is the receiver bandwidth. Once the amplitude is determined, the area of the gradient is just the product of the amplitude with its time duration. The area of the dephaser gradient is about half the area of the readout gradient (see, e.g., FIG. 4A).

Figure 6:
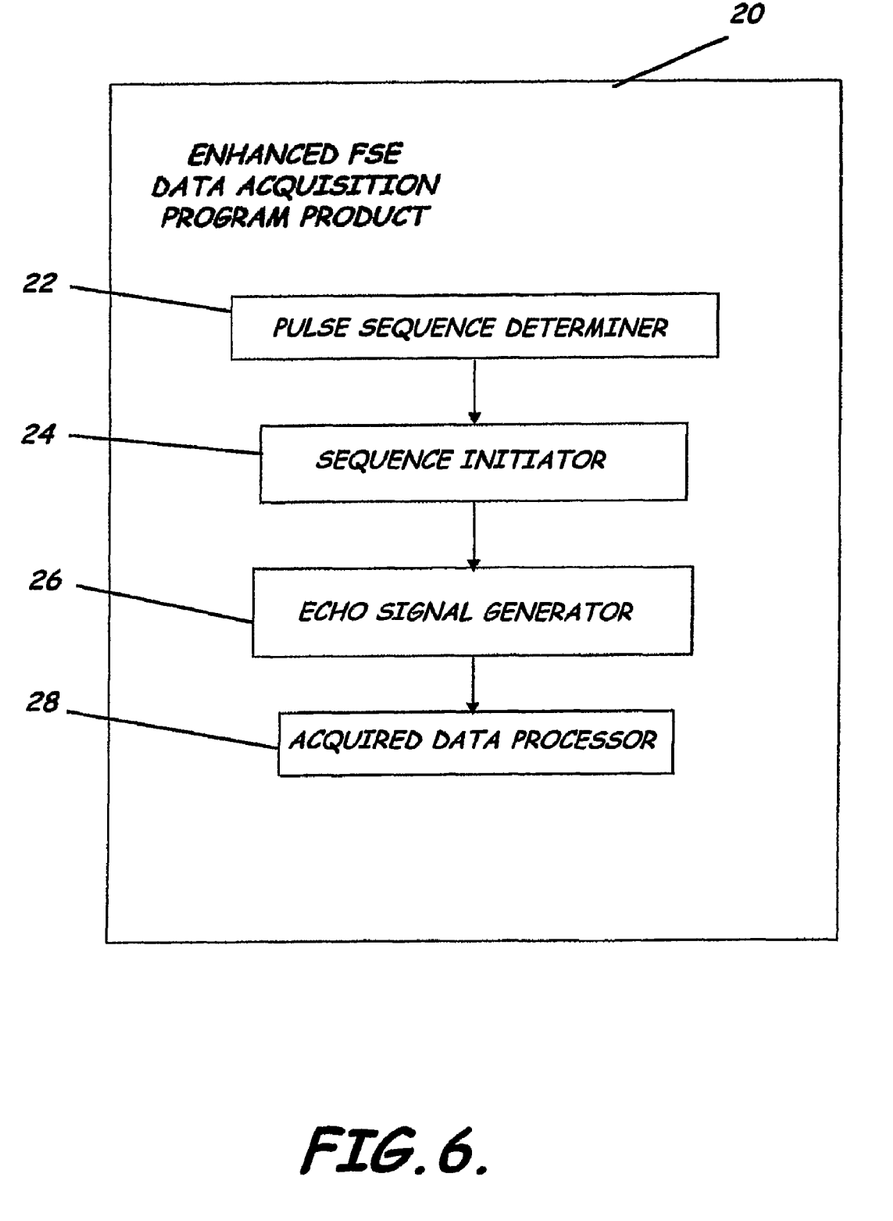
FIG. 6 is a schematic diagram of a program product for a magnetic resonant imaging system according to an embodiment of the present invention.

Also in this example, the plurality of echo signals includes a first, a second, and a third echo signal occurring sequentially in time and corresponding to the respective first, second, and the third readout gradient pulses. Each of the first, the second, and the third echo signals is phase encoded identically. As shown in FIGS. 6 and 8, the method can also include selecting a field of view and an acquisition matrix size for a desired resolution (block 53), determining a receiver bandwidth so that the total readout time for each esp corresponds to about the time it takes for water and fat signals to become opposed phased (block 55), and calculating an amplitude of the first, second, and third readout gradient pulses (block 57). These steps preferably occur prior to initiating the pulse sequence such as by a sequence initiator 24 as described herein in an MRI system 10, but alternatively, as understood by those skilled in the art, can also be interactive-type steps to further enhance and achieve desired results.

For example, this calculation to determine amplitude of a readout gradient responsive to a desired receiver bandwidth (FIG. 8) can be accomplished, for example, by using a pulse sequence determiner 22 as a modification to conventional pulse sequence programs or software as understood by those skilled in the art. After the amplitude is determined, then each of the plurality of readout gradient pulses initiated by the sequence initiator 24 can advantageously have the same amplitude, and the plurality of echo signals generated by an echo signal generator 26 correspond to plurality of readout gradient pulses. As understood by those skilled in the art, the acquired data from the echo signals can be processed such as by an acquired data processor 28 (see FIG. 6) to thereby produce the desired images.

The method further can include repeating the steps of initiating a gradient pulse sequence and collecting a plurality of echo signals for each of a plurality of substantially equal and sequential esp time periods, which is substantially equal to the esp time period, e.g., between successive 180 degree RF pulses in an FSE echo train. As understood by those skilled in the art, each set of the first, the second, and the third echo signals, which is generated between each of the successive echo spacing time periods, is phase coded differently to acquire a complete set of data to form images. The method also can include forming three images corresponding to the set of the first, the second, and the third echo signals.

As illustrated in FIGS. 1, 3-8, embodiments of a program product 20 or software, as understood by those skilled in the art, stored in a tangible computer medium to be operable on a computer are also provided to enhance data acquisition and processing. The program product 20 operates to perform the steps of initiating a gradient pulse sequencing during an echo spacing (esp) time period. The gradient pulse sequencing has a plurality of readout gradient pulses that use substantially all of the esp time period. The operating steps also can include collecting a plurality of echo signals during the esp time period responsive to the plurality of readout gradient pulses. Each of the plurality of echo signals corresponding to one of the plurality of readout gradient pulses, and the plurality of echo signals likewise being generated to use substantially all of the esp time period. The other steps of the program product are described above with respect to the method as understood by those skilled in the art and are not repeated herein for brevity.

The centers of gxw− and gxw+ are shifted by τ to before and after the center of gxw, respectively. In an embodiment, for example, τ may be conveniently set to a time that will cause water and fat signals to be out of phase by 180° at 1.5 Tesla, or 540° at 3.0 Tesla. In these cases, τ is approximately 2.3 milliseconds (ms) at 1.5 Tesla and 3.45 ms at 3.0 Tesla. In comparison to the conventional fast spin (FSE) echo, three echoes can be formed during each esp period. These three echoes are phase encoded identically. Like in the conventional fast spin echo, echoes from different esp periods are still phase encoded differently. As a result, three images (corresponding to the echoes by gxw−, gxw, and gxw+, respectively) can now be formed.

For example, using $S_-$, $S$, and $S_+$ to represent the three images corresponding to gxw−, gxw, and gxw+, these images can be expressed as:

$$S_- = (W-F)e^{-R_2 TE} e^{(-R'_2 + R_2)\tau} e^{i(\phi_o - \phi)} \quad [1]$$

$$S_+ = (W-F)e^{-R_2 TE} e^{(-R'_2 - R_2)\tau} e^{i(\phi_o + \phi)} \quad [2]$$

$$S = (W+F)e^{-R_2 TE} e^{i\phi_o} \quad [3]$$

where W and F are the real and non-negative variables representing magnitudes of the respective magnetization vectors of water and fat, and TE is the echo time, or the time between the 90° excitation pulse and the center of the gxw that has zero phase encode gradient (see FIG. 4). $R_2$ ($=1/T_2$) and $R'_2$ ($=1/T'_2$) are the RF irreversible and RF reversible components of the transverse relaxation rate constants. Another related parameter that can be obtained, once $R_2$ and $R'_2$ are determined, is $R^*_2$ which is the simply the sum of $R_2$ and $R'_2$.

Also, if we define:

$$P_o = e^{i\phi_o} \quad [4]$$

$$P_1 = e^{i\phi} \quad [5]$$

where $P_0$ and $P_1$ are unknown phasors representing phase errors, then:

$$P_o = \frac{S}{|S|} \quad [6]$$

where | . . . | represents taking the absolute value. $P_o$ can be removed from Eqs. [1-3]:

$$\bar{S}_- = S_- P^*_o = (W-F)e^{-R_2 TE} e^{(-R'_2 + R_2)\tau} e^{-i\phi} \quad [7]$$

$$\bar{S}_+ = S_+ P^*_o = (W-F)e^{-R_2 TE} e^{(-R'_2 - R_2)\tau} e^{-i\phi} \quad [8]$$

$$\bar{S} = SP^*_o = (W+F)e^{-R_2 TE} \quad [9]$$

where * represents taking the complex conjugate. Two different approaches can be taken to determine $e^{i\phi}$ (or $P_1$). The first approach is to take the average of Eq. [7] and Eq. [8]:

$$S_\pm = \frac{[\bar{S}_+ + (\bar{S}_-)^*]}{2} \quad [10]$$

$$= (W-F)e^{-R_2 TE} e^{i\phi} \frac{e^{(-R'_2 - R_2)\tau} + e^{(-R'_2 + R_2)\tau}}{2}$$

To a very good approximation, the last term in Eq. [10] is equal to 1. Therefore:

$$S_\pm = (W-F)e^{-R_2 TE} e^{i\phi} \quad [11]$$

A phase correction method, such as that described in co-pending U.S. patent application Ser. No. 10/997,826, filed on Nov. 24, 2004, titled "A Highly Efficient and Highly Robust Method for Phase Correction," and which is incorporated herein by reference in its entirety, can be used, as understood by those skilled in the art, to further process the data and determine $e^{i\Phi}$ (or $P_1$), and after which to determine:

$$S'_\pm = S_\pm P^*_1 = (W-F)e^{-R_2 TE} \quad [12]$$

From Eq. [9] and Eq. [12], a T2-weighted water-only image and T2-weighted fat-only image can be calculated as follows:

$$W' = We^{-R_2 TE} = \frac{\bar{S} + S'_\pm}{2} \quad [13]$$

$$F' = Fe^{-R_2 TE} = \frac{\bar{S} - S'_\pm}{2} \quad [14]$$

A second approach is to use the above phase correction method and Eq. [7] and Eq. [8] separately to determine $e^{i\Phi}$ (or $P_1$). Combining phase-corrected Eq. [7] with Eq. [9] will lead to a set of solutions for W and F. Combining phase corrected Eq. [8] with Eq. 9] will lead to a second set of solutions for W and F. These two sets of solutions can then be averaged to produce a final set of solutions for W and F.

In order to determine $R_2$, we can take the absolute value of the ratio of Eq. [2] over Eq. [1]:

$$e^{-2R_2\tau} = \left|\frac{S_+}{S_-}\right| \quad [15]$$

and from which Eq. [14] can be calculated as:

$$R_2 = -\frac{1}{2\tau}\ln\left(\left|\frac{S_+}{S_-}\right|\right) \quad [16]$$

One way to determine $R'_2$ is given as follows:

$$\frac{\sqrt{|S_-|\cdot|S_+|}}{|S|} = \frac{|(W-F)|e^{-R_2 TE}}{(W+F)e^{-R_2 TE}}e^{-R'_2\tau} = \frac{|(W'-F')|}{(W'+F')}e^{-R'_2\tau} \quad [17]$$

which leads to:

$$R'_2 = -\frac{1}{\tau}\ln\left\{\frac{\sqrt{|S_-|\cdot|S_+|}}{|S|} \cdot \frac{(W'+F')}{|(W'-F')|}\right\}$$

where W' and F' are given in Eqs. [13] and [14].

Figure 7:
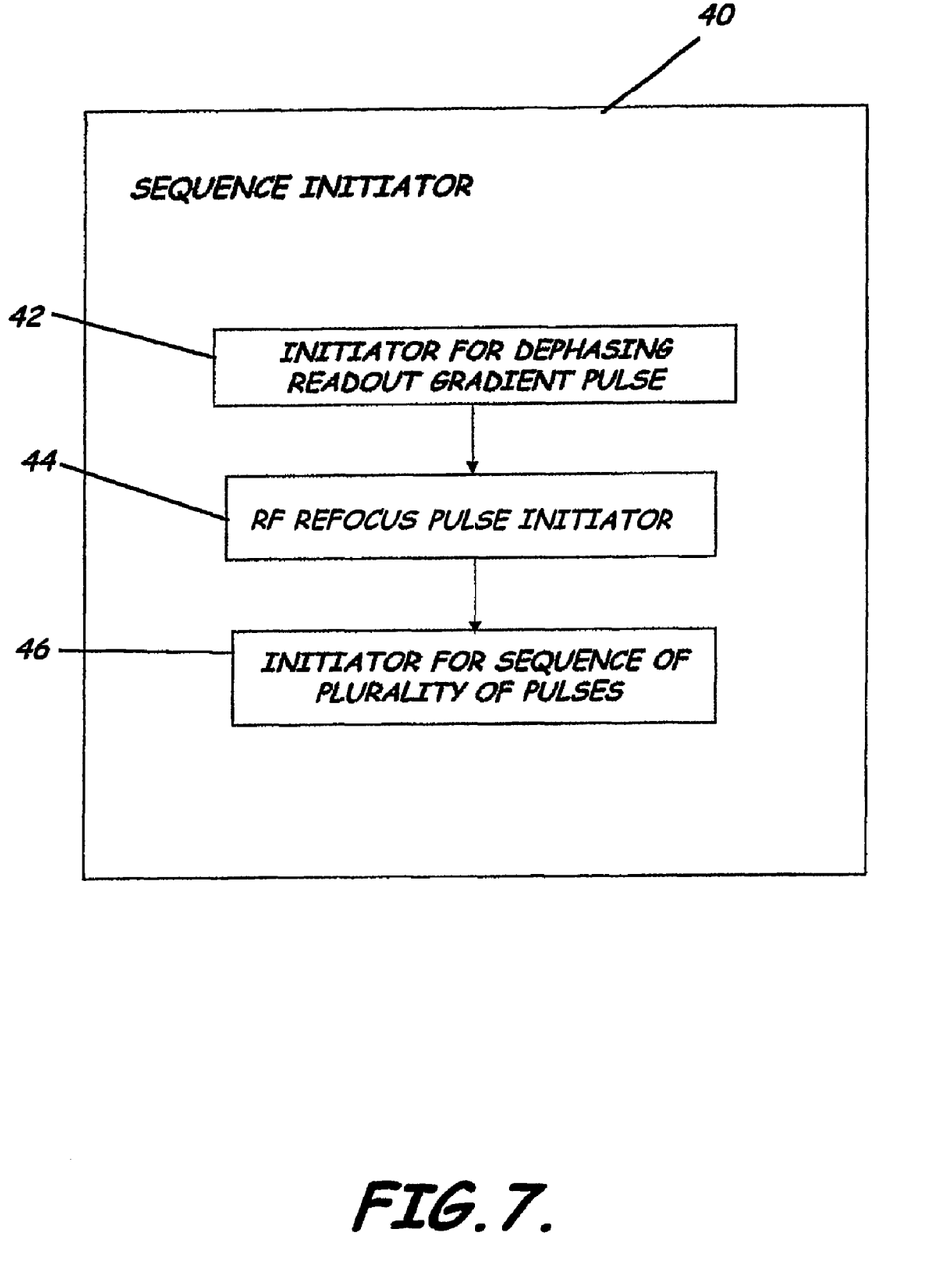
FIG. 7 is a schematic diagram of a program product according to an embodiment of the present invention.

Still another embodiment of the present invention provides a program product stored in a tangible computer medium to be operable on a computer. As shown in FIGS. 6-7, the program product 40, e.g., such as by a type of or an embodiment of a sequence initiator 24 (FIG. 6), operates to perform the step of initiating an initial dephasing gradient pulse (block 42) along a readout gradient axis prior in time to an occurrence of a first radio frequency (RF) refocus pulse being initiated along a readout gradient axis (block 44) prior in time to an occurrence of a first radio frequency (RF) refocus pulse being initiated along an RF axis. The initial dephasing gradient pulse has a first gradient area defined by the product of an amplitude of the dephasing pulse and a time duration of the dephasing pulse. The operating also including the step of initiating a plurality of readout gradient pulses (block 46) later in time than the first RF refocus pulse and prior in time to a second RF refocus pulse. The lapse of time between the first RF refocus pulse and the second RF refocus pulse defines an echo spacing (esp) time period. Each of the plurality of readout gradient pulses has a second gradient area also defined by the product of an amplitude of the readout gradient pulse and a time duration of the same readout gradient pulse. An absolute value of the second gradient area is equal to about two times the first gradient area. The operating steps can further include collecting a plurality of echo signals during the esp time period responsive to the plurality of readout gradient pulses. Each of the plurality of echo signals corresponds to one of the plurality of readout gradient pulses. As understood by those skilled in the art, this, again, is then repeated for each of the pairs of RF refocus pulses in an FSE echo train.

Although the invention has been particularly shown as described with reference to embodiments herein, it will be understood by those skilled in the art that various changes in form and detail can be made therein without departing from the spirit and scope of the invention. For example, it will be appreciated that the concepts disclosed herein can be extended or modified to apply to other types of configuration constructs having different rules than the particular exemplary embodiments disclosed herein. In addition, although aspects of the present invention have been described with respect to a computer, a computer device, a computer system, or controller executing software that directs the functions of embodiments of the present invention, it should be understood by those skilled in the art that present invention can alternatively be implemented as a program product for use with various types of data processing systems as well. Programs defining the functions of embodiments of the present invention, for example, can be delivered to a data processing system via a variety of signal-bearing media, which include, without limitation, non-rewritable storage media (e.g., CD-ROM, DVD-ROM), rewritable storage media (e.g., a floppy diskette, hard disk drive, or rewritable ROM media), and communication media, such as digital and analog networks. It should be understood, therefore, that such signal-bearing media, when carrying or encoding computer readable instructions that direct the functions of embodiments of the present invention, represent alternative embodiments of the present invention.

The invention has been sufficiently described so that a person with average knowledge in the matter may reproduce and obtain the results mentioned in the invention herein. Nonetheless, any skilled person in the field of technique, subject of the invention herein, may carry out modifications not described herein, to apply these modifications to a determined structure, or in the manufacturing process of the same, requires the claimed matter in the following claims; such structures also shall be covered within the scope of the invention. In the drawings and specification, there have been disclosed embodiments of the invention and, although specific terms are employed, they are used in a generic and descriptive sense only and not for the purpose of limitation, the scope of the invention being set forth in the following claims.

That claimed is:

1. A system to acquire data in a single magnetic resonant imaging (MRI) scan, the system comprising:
   an MRI device adapted to provide an MRI scan of a subject;
   a controller associated with the MRI device to control the scanning of the MRI device;

memory associated with the controller and having program product stored therein, the program product operating to perform the steps of:
- (a) initiating an initial dephasing gradient pulse along a readout gradient axis prior in time to an occurrence of a first radio frequency (RF) refocus pulse being initiated along an RF axis, the initial dephasing gradient pulse having a first gradient area defined by the product of an amplitude of the dephasing pulse and a time duration of the dephasing pulse,
- (b) initiating a plurality of readout gradient pulses later in time than the first RF refocus pulse and prior in time to a second RF refocus pulse, the lapse of time between the first RF refocus pulse and the second RF refocus pulse defining an echo spacing (esp) time period, each of the plurality of readout gradient pulses having a second gradient area also defined by the product of an amplitude of the readout gradient pulse and a time duration of the same readout gradient pulse, an absolute value of the second gradient area being equal to about two times the first gradient area, and
- (c) collecting a plurality of echo signals during the esp time period responsive to the plurality of readout gradient pulses, each of the plurality of echo signals corresponding to one of the plurality of readout gradient pulses; and a display responsive to the controller to display one or more magnetic resonant images.

2. A system as defined in claim 1, wherein the program product further operates to perform the steps of initiating an excitation pulse along the RF axis prior in time to the occurrence of the initial dephasing gradient pulse and to the occurrence of the first RF refocus pulse and, responsive to the generated plurality of echo signals, determining one or more of spatial distribution of water, spatial distribution of fat, and spatial distribution of transverse relaxation time constants.

3. A system as defined in claim 1, wherein the plurality of readout gradient pulses comprises a respective first, a second, and a third readout gradient pulses occurring sequentially in time, wherein the second gradient area of each of the first, the second, and the third readout gradient pulses being substantially equal, wherein the respective time duration of each of the first, the second, and the third readout gradient pulse is substantially equal, and wherein a center of the esp time period substantially corresponds to a center of the second readout gradient pulse.

4. A system as defined in claim 3, wherein a time shift between a center of the first readout gradient pulse and the center of the second readout gradient pulse defines a user-selected time shift ($\ddot{y}$), and wherein a time shift between the center of the second readout gradient pulse and a center of the third readout gradient pulse also substantially equals $\ddot{y}$, $\ddot{y}$ being set by a user so that water data signals and fat data signals being generated responsive to the first readout gradient pulse and responsive to the third readout gradient pulse have a pre-selected phase angle.

5. A system as defined in claim 3, wherein the first and third readout gradient pulses have the same polarity as the initial dephasing gradient pulse, and wherein the second readout gradient pulse has an opposite polarity to the initial dephasing gradient pulse.

6. A system as defined in claim 3, wherein the plurality of echo signals comprises a first, a second, and a third echo signal occurring sequentially in time and corresponding to the respective first, second, and the third readout gradient pulses, each of the first, the second, and the third echo signals being phase encoded identically.

7. A system as defined in claim 6, wherein the program product operates to further perform the steps of repeating the steps of initiating the initial dephasing gradient pulse and initiating the plurality of readout gradient pulses for each of a plurality of substantially equal and sequential esp time periods, each being substantially equal to the esp time period, each set of the first, the second, and the third echo signals being generated between each of the sequential preselected time periods being phase coded differently, forming three images on the display corresponding to the set of the first, the second, and the third echo signals, and processing the three images corresponding to the first, the second, and the third echo signals to generate images of separate water, separate fat, and transverse relaxation times.

* * * * *